(12) United States Patent
Lalli et al.

(10) Patent No.: US 11,931,002 B2
(45) Date of Patent: Mar. 19, 2024

(54) SLEEVE FOR SPECULUM AND USE THEREOF

(71) Applicant: CEEK Women's Health, Inc., Portland, OR (US)

(72) Inventors: Maria Lalli, Portland, OR (US); Fahti Self, Portland, OR (US); Darius Naigamwalla, Portland, OR (US)

(73) Assignee: CEEK Women's Health, Inc., Portland, OR (US)

( * ) Notice: Subject to any disclaimer, the term of this patent is extended or adjusted under 35 U.S.C. 154(b) by 0 days.

(21) Appl. No.: 17/235,714

(22) Filed: Apr. 20, 2021

(65) Prior Publication Data

US 2022/0087512 A1     Mar. 24, 2022

Related U.S. Application Data

(63) Continuation of application No. 15/393,041, filed on Dec. 28, 2016, now abandoned.
(Continued)

(51) Int. Cl.
| | | |
|---|---|---|
| *A61B 1/00* | (2006.01) |
| *A61B 1/303* | (2006.01) |
| *A61B 1/32* | (2006.01) |
| *A61B 5/00* | (2006.01) |
| *A61B 10/02* | (2006.01) |
| *A61B 17/43* | (2006.01) |
| *A61B 18/00* | (2006.01) |
| *A61B 50/30* | (2016.01) |

(Continued)

(52) U.S. Cl.
CPC ...... *A61B 1/00135* (2013.01); *A61B 1/00103* (2013.01); *A61B 1/303* (2013.01); *A61B 1/32* (2013.01); *A61B 5/4337* (2013.01); *A61B 10/0291* (2013.01); *A61B 17/43* (2013.01); *A61B 50/30* (2016.02); *A61B 90/04* (2016.02); *A61F 6/18* (2013.01); *A61B 2018/00559* (2013.01)

(58) Field of Classification Search
CPC . A61B 1/00135; A61B 1/00103; A61B 1/303; A61B 1/32; A61B 90/04; A61F 6/18
USPC ................................................ 600/201–245
See application file for complete search history.

(56) References Cited

U.S. PATENT DOCUMENTS

| 55,511 A | 6/1866 | Lentz |
| 977,489 A | 12/1910 | Unruh |

(Continued)

FOREIGN PATENT DOCUMENTS

| AU | 2016380985 A1 | 7/2018 |
| CN | 201595813 U | 10/2010 |

(Continued)

*Primary Examiner* — Eduardo C Robert
*Assistant Examiner* — Tara Rose E Carter
(74) *Attorney, Agent, or Firm* — Mintz, Levin, Cohn, Ferris, Glovsky and Popeo, P.C.

(57) ABSTRACT

An accessory sleeve and a method for use is provided. The accessory sleeve includes a cylindrical sleeve body. The cylindrical sleeve body includes an outer surface, an inner surface, the inner surface defining a hollow sleeve channel, and at least one open end. The sleeve body is configured to receive an insertion portion of a medical speculum in the hollow sleeve channel, and the sleeve body is further configured to expand from a first state to a second state.

20 Claims, 9 Drawing Sheets

Related U.S. Application Data

(60) Provisional application No. 62/310,607, filed on Mar. 18, 2016, provisional application No. 62/281,695, filed on Jan. 21, 2016, provisional application No. 62/272,621, filed on Dec. 29, 2015.

(51) Int. Cl.
   *A61B 90/00* (2016.01)
   *A61F 6/18* (2006.01)

(56) References Cited

U.S. PATENT DOCUMENTS

| | | |
|---|---|---|
| 1,969,671 A | 8/1934 | Archer |
| 2,083,573 A | 6/1937 | Morgan |
| 2,123,343 A | 7/1938 | Rightsell |
| 2,324,485 A | 7/1943 | Chamberlain |
| 2,509,241 A | 5/1950 | Mende |
| 2,512,434 A | 6/1950 | Anton |
| 2,579,849 A | 12/1951 | Newman |
| 2,670,736 A | 3/1954 | Dunkelberger |
| 2,714,886 A | 8/1955 | Charles |
| 2,884,925 A | 5/1959 | Meynier |
| 2,954,025 A | 9/1960 | Grieshaber |
| 3,110,305 A | 11/1963 | Sygnator |
| 3,139,886 A | 7/1964 | Tallman et al. |
| 3,246,646 A | 4/1966 | Murphy, Jr. |
| 3,324,850 A | 6/1967 | Emmett et al. |
| 3,332,414 A | 7/1967 | Gasper |
| 3,532,088 A | 10/1970 | Fiore |
| 3,565,061 A | 2/1971 | Reynolds |
| 3,650,266 A | 3/1972 | Pestka et al. |
| 3,744,481 A | 7/1973 | McDonald |
| 3,752,149 A | 8/1973 | Rosenthal et al. |
| 3,762,400 A | 10/1973 | McDonald |
| 3,769,968 A | 11/1973 | Blount et al. |
| 3,815,585 A | 6/1974 | Fiore |
| 3,841,317 A | 10/1974 | Awais |
| 3,851,642 A | 12/1974 | McDonald |
| 3,857,395 A | 12/1974 | Johnson et al. |
| 3,885,563 A | 5/1975 | Johnson et al. |
| 3,890,961 A | 6/1975 | Moore et al. |
| 4,004,591 A | 1/1977 | Freimark |
| 4,010,751 A | 3/1977 | Ring |
| 4,344,419 A | 8/1982 | Burgin |
| 4,356,817 A | 11/1982 | McKibben et al. |
| 4,428,370 A | 1/1984 | Keely |
| 4,492,220 A | 1/1985 | Hayes |
| 4,502,468 A | 3/1985 | Burgin |
| 4,566,439 A | 1/1986 | Burgin |
| 4,597,382 A | 7/1986 | Perez, Jr. |
| 4,638,792 A | 1/1987 | Burgin |
| 4,676,773 A | 6/1987 | Sheldon |
| 4,735,621 A | 4/1988 | Hessel |
| D299,532 S | 1/1989 | Cecil et al. |
| 4,805,604 A | 2/1989 | Spery |
| 4,807,600 A | 2/1989 | Hayes |
| 4,834,077 A | 5/1989 | Sun |
| 4,857,175 A | 8/1989 | Spinnler |
| 4,867,176 A | 9/1989 | Lash |
| 4,945,923 A | 8/1990 | Evans et al. |
| 4,976,273 A | 12/1990 | Hessel |
| 4,981,147 A | 1/1991 | Barnett |
| 4,984,564 A | 1/1991 | Yuen |
| 4,993,433 A | 2/1991 | Reddy |
| 5,007,409 A | 4/1991 | Pope |
| 5,041,080 A | 8/1991 | Shimatani et al. |
| 5,072,720 A | 12/1991 | Francis et al. |
| 5,083,414 A | 1/1992 | Wu |
| 5,094,250 A | 3/1992 | Hessel |
| 5,135,475 A | 8/1992 | Nakanishi et al. |
| 5,156,165 A | 10/1992 | Wu |
| 5,174,278 A | 12/1992 | Babkow |
| 5,179,936 A | 1/1993 | Ohara et al. |
| 5,179,937 A | 1/1993 | Lee |
| 5,193,555 A | 3/1993 | Richardson et al. |
| 5,209,241 A | 5/1993 | Hardy |
| 5,243,966 A | 9/1993 | Ng |
| 5,342,385 A | 8/1994 | Norelli et al. |
| 5,347,995 A | 9/1994 | Slater et al. |
| 5,377,667 A | 1/1995 | Patton et al. |
| 5,433,219 A | 7/1995 | Spery |
| 5,460,165 A | 10/1995 | Mayes |
| 5,505,690 A | 4/1996 | Patton et al. |
| 5,540,658 A | 7/1996 | Evans et al. |
| 5,598,852 A | 2/1997 | Spery |
| 5,622,185 A | 4/1997 | Richardson et al. |
| 5,623,946 A | 4/1997 | Hessel |
| 5,687,741 A | 11/1997 | Torger |
| 5,716,329 A | 2/1998 | Dieter |
| 5,743,852 A | 4/1998 | Johnson |
| 5,785,648 A | 7/1998 | Min |
| 5,865,729 A | 2/1999 | Meehan et al. |
| 5,868,668 A | 2/1999 | Weiss |
| 5,992,415 A | 11/1999 | Alla et al. |
| 6,019,743 A | 2/2000 | Cole et al. |
| 6,024,696 A | 2/2000 | Hoftman et al. |
| 6,036,638 A | 3/2000 | Nwawka |
| 6,048,308 A | 4/2000 | Strong |
| 6,095,998 A | 8/2000 | Osborn et al. |
| 6,096,046 A | 8/2000 | Weiss |
| 6,174,282 B1 | 1/2001 | Tan |
| 6,186,973 B1 | 2/2001 | Buzot |
| 6,248,089 B1 | 6/2001 | Porat |
| 6,254,566 B1 | 7/2001 | Buck et al. |
| 6,280,379 B1 | 8/2001 | Resnick |
| 6,287,251 B1 | 9/2001 | Tan |
| 6,302,862 B1 | 10/2001 | Osborn et al. |
| 6,341,607 B1 | 1/2002 | Couvreur |
| 6,347,243 B1 | 2/2002 | Fraden |
| 6,354,995 B1 | 3/2002 | Hoftman et al. |
| 6,361,543 B1 | 3/2002 | Chin et al. |
| 6,379,299 B1 | 4/2002 | Borodulin et al. |
| 6,395,012 B1 | 5/2002 | Yoon et al. |
| 6,416,466 B1 | 7/2002 | Hsiao |
| 6,416,467 B1 | 7/2002 | Mcmillin et al. |
| 6,428,474 B1 | 8/2002 | Weiss |
| 6,432,048 B1 | 8/2002 | Francois |
| 6,436,033 B2 | 8/2002 | Tan |
| 6,508,780 B1 | 1/2003 | Edgett et al. |
| D474,275 S | 5/2003 | Tan |
| 6,569,091 B2 | 5/2003 | Diokno et al. |
| 6,669,654 B2 | 12/2003 | Diokno et al. |
| 6,702,740 B2 | 3/2004 | Herold |
| 6,902,530 B1 | 6/2005 | Pianka |
| 6,939,289 B2 | 9/2005 | Zunker et al. |
| 7,047,975 B2 | 5/2006 | Austin et al. |
| 7,063,664 B2 | 6/2006 | Mohajer |
| 7,105,007 B2 | 9/2006 | Hibler |
| 7,172,573 B1 | 2/2007 | Lamb |
| 7,311,663 B2 | 12/2007 | Marcotte |
| D558,871 S | 1/2008 | Osterberg et al. |
| 7,322,358 B2 | 1/2008 | Tam et al. |
| 7,338,462 B2 | 3/2008 | Minoguchi et al. |
| 7,371,212 B2 | 5/2008 | Klaassen |
| 7,392,807 B2 | 7/2008 | Osterberg |
| D593,195 S | 5/2009 | Osterberg |
| 7,654,953 B2 | 2/2010 | Borodulin et al. |
| 7,658,712 B2 | 2/2010 | Klaassen et al. |
| 7,665,893 B2 | 2/2010 | Buchalter |
| 7,798,986 B2 | 9/2010 | Melvin et al. |
| 7,810,500 B2 | 10/2010 | Osterberg |
| 7,815,594 B2 | 10/2010 | Dougherty et al. |
| 7,896,806 B2 | 3/2011 | Shah et al. |
| 7,918,004 B2 | 4/2011 | Melvin et al. |
| 8,062,245 B2 | 11/2011 | Gann et al. |
| 8,075,512 B2 | 12/2011 | Sargent et al. |
| 8,083,673 B2 | 12/2011 | Rosen |
| 8,142,352 B2 | 3/2012 | Vivenzio et al. |
| 8,162,872 B2 | 4/2012 | Loyd et al. |
| 8,256,423 B2 | 9/2012 | Osterberg |
| 8,267,860 B2 | 9/2012 | Klaassen et al. |
| D671,642 S | 11/2012 | Grisby |
| 8,435,205 B2 | 5/2013 | Arora et al. |

(56) References Cited

U.S. PATENT DOCUMENTS

| | | |
|---|---|---|
| 8,449,491 B2 | 5/2013 | Hasse et al. |
| 8,449,492 B2 | 5/2013 | Sargent et al. |
| 8,460,187 B2 | 6/2013 | Bouquet |
| 8,485,196 B2 | 7/2013 | Osterberg |
| 8,539,660 B2 | 9/2013 | Melvin et al. |
| 8,652,035 B2 | 2/2014 | Steigerwald |
| 8,734,414 B2 | 5/2014 | Winkel et al. |
| 8,747,308 B2 | 6/2014 | Muzzammel |
| D710,500 S | 8/2014 | Roeloffs |
| 8,834,362 B2 | 9/2014 | Shipp |
| 8,876,711 B2 | 11/2014 | Lin et al. |
| 8,926,547 B2 | 1/2015 | Arora et al. |
| 8,979,751 B2 | 3/2015 | George |
| 8,979,851 B2 | 3/2015 | Fallin et al. |
| 9,132,043 B2 | 9/2015 | Winkel et al. |
| 9,186,282 B2 | 11/2015 | Ito et al. |
| 9,233,029 B2 | 1/2016 | Gann et al. |
| 9,283,122 B2 | 3/2016 | Taniguchi et al. |
| 9,326,671 B2 | 5/2016 | Roeloffs |
| 10,456,016 B2 | 10/2019 | Lalli et al. |
| 10,687,699 B2 | 6/2020 | Lalli et al. |
| D924,397 S | 7/2021 | Lalli et al. |
| 11,147,444 B2 | 10/2021 | Vella et al. |
| D935,610 S | 11/2021 | Wang et al. |
| D986,415 S | 5/2023 | Lalli et al. |
| 2001/0056223 A1 | 12/2001 | Thompson |
| 2002/0115910 A1 | 8/2002 | Diokno et al. |
| 2003/0069477 A1 | 4/2003 | Raisman et al. |
| 2003/0105387 A1 | 6/2003 | Frumovitz et al. |
| 2005/0021069 A1 | 1/2005 | Feuer et al. |
| 2005/0021080 A1 | 1/2005 | Feuer et al. |
| 2005/0085699 A1 | 4/2005 | Weiss |
| 2005/0124860 A1 | 6/2005 | Mohajer |
| 2005/0192482 A1 | 9/2005 | Carpenter et al. |
| 2005/0197615 A1 | 9/2005 | Gann et al. |
| 2005/0273044 A1 | 12/2005 | Gann et al. |
| 2005/0277867 A1 | 12/2005 | Minoguchi et al. |
| 2006/0047285 A1 | 3/2006 | Fields |
| 2006/0079924 A1 | 4/2006 | Sanders et al. |
| 2006/0084843 A1 | 4/2006 | Sommerich et al. |
| 2006/0122463 A1 | 6/2006 | Klaassen |
| 2007/0032758 A1 | 2/2007 | Chase et al. |
| 2007/0032814 A1 | 2/2007 | Hibler |
| 2007/0156022 A1 | 7/2007 | Patel |
| 2008/0058605 A1 | 3/2008 | Sorensen |
| 2008/0114210 A1 | 5/2008 | Shah et al. |
| 2008/0242938 A1 | 10/2008 | Larkin |
| 2008/0262407 A1 | 10/2008 | Chase et al. |
| 2008/0287744 A1 | 11/2008 | Borodulin et al. |
| 2008/0306345 A1 | 12/2008 | Balas |
| 2009/0062691 A1 | 3/2009 | Kim |
| 2009/0099422 A1 | 4/2009 | George |
| 2009/0326331 A1 | 12/2009 | Rosen |
| 2011/0009803 A1 | 1/2011 | Dougherty et al. |
| 2011/0040234 A1 | 2/2011 | Chaffringeon |
| 2011/0237902 A1 | 9/2011 | Rosen |
| 2012/0220918 A1 | 8/2012 | Chaffringeon |
| 2013/0197314 A1 | 8/2013 | Eakin |
| 2014/0081281 A1 | 3/2014 | Felder |
| 2014/0109915 A1 | 4/2014 | Reddy et al. |
| 2014/0163322 A1 | 6/2014 | Mehta |
| 2015/0057502 A1 | 2/2015 | George |
| 2015/0112148 A1 | 4/2015 | Bouquet |
| 2015/0290440 A1 | 10/2015 | Redol |
| 2017/0181605 A1 | 6/2017 | Lalli et al. |
| 2017/0181607 A1 | 6/2017 | Lalli et al. |
| 2017/0181615 A1 | 6/2017 | Vella et al. |
| 2017/0181616 A1 | 6/2017 | Vella et al. |
| 2018/0263480 A1 | 9/2018 | Lalli et al. |
| 2022/0095898 A1 | 3/2022 | Lalli et al. |
| 2022/0104699 A1 | 4/2022 | Self et al. |
| 2022/0175239 A1 | 6/2022 | Vella et al. |

FOREIGN PATENT DOCUMENTS

| | | | |
|---|---|---|---|
| CN | 201996970 U | 10/2011 | |
| EM | 008460802-0002 A1 | 3/2021 | |
| EM | 008460802-0003 A1 | 3/2021 | |
| EM | 008460802-0004 A1 | 3/2021 | |
| EM | 008460802-0005 A1 | 3/2021 | |
| EM | 008460802-0006 A1 | 3/2021 | |
| EM | 008460802-0007 A1 | 3/2021 | |
| EM | 0084608020001 A1 | 3/2021 | |
| GB | 2424585 A | 10/2006 | |
| GB | 2459076 A | 10/2009 | |
| GB | 6123744 | 3/2021 | |
| GB | 6123745 | 3/2021 | |
| GB | 6123747 | 3/2021 | |
| WO | 19981181 | 3/1998 | |
| WO | WO-9833431 A1 * | 8/1998 | ......... A61B 1/00135 |
| WO | 2009000078 A1 | 12/2008 | |
| WO | 2011024901 A1 | 3/2011 | |
| WO | 2017117308 A2 | 7/2017 | |
| WO | 2017117310 A2 | 7/2017 | |
| WO | 2017117312 A2 | 7/2017 | |
| WO | 2017117313 A2 | 7/2017 | |
| WO | 2020076967 A1 | 4/2020 | |

* cited by examiner

SLEEVE FOR SPECULUM AND USE THEREOF

CROSS-REFERENCE TO RELATED PATENT APPLICATIONS

This application is a continuation of U.S. patent application Ser. No. 15/393,041 filed Dec. 28, 2016, entitled "Sleeve for Speculum and Use Thereof," which claims the benefit of and priority to U.S. Provisional Patent Application No. 62/272,621 filed Dec. 29, 2015, entitled "Modifier Sleeve for Speculum and Use Thereof," U.S. Provisional Patent Application No. 62/281,695 filed Jan. 21, 2016, entitled "Modifier Sleeve for Speculum and Use Thereof," and U.S. Provisional Patent Application No. 62/310,607 filed Mar. 18, 2016, entitled "Modifier Sleeve for Speculum and Use Thereof." Each of the aforementioned patent applications is incorporated herein by reference in its entirety.

BACKGROUND

The present invention relates generally to the field of a medical speculum.

A speculum is a medical tool used to provide visualization into a body cavity. Speculums or specula are traditionally used for viewing and accessing the vaginal cavity for gynecology patients. The traditional speculum consists of two blades with a hinge and a handle. The blades are inserted into the body cavity in a closed position, and separated by squeezing two pieces of the handle together or applying force to a lever attached to the handle, thereby dilating the vagina and providing visualization of and accessibility to the vagina, the cervix, and surrounding areas. Once opened, the speculum can be locked in an open position, e.g., by using a screw-based mechanism so an operator (e.g., physician, nurse, mid-wife, etc.) does not need to continue squeezing the pieces of the handle or the lever during the inspection. The operator can then proceed with inspecting the vagina, conducting a Pap smear, or any other medical procedures that may need to be provided.

The double blade design of speculum devices has been in use since the 1800s, and few changes have been made to the original design. The biggest changes with the double blade design have been changes in the material from metal to plastic and the addition of internal lighting on some models of the speculum so that the operator does not have to rely on external lighting to gain a clear view of the vagina and the cervix.

A few, less widely used alternative speculum designs exist. About fifteen years ago, an inflatable speculum was developed, but it failed to gain any traction in the market and was quickly discontinued. The inflatable speculum was inserted into the vagina, and air was used to inflate a tube of the speculum to open the vaginal canal and exert pressure equally on all sides of the canal. However, there were a number of problems with this concept: (1) The tube filled the entire cavity and prevented the operator from seeing the vaginal walls, which can be useful for diagnosing infections or lesions. (2) The inflation technology used to operate the device included an extremely noisy inflatable pump mechanism that increased patient anxiety and discomfort during the examination process (though other traditional speculum designs also employ mechanisms that are noisy to manipulate and actuate, and create patient anxiety during a procedure). Another alternative speculum design includes a stopper that prevents air from leaving the vagina upon insertion of the speculum into the vagina. Air can then be pumped inside the vagina to open the vagina during examination. However, this method relies on cameras for viewing because having a viewing opening between the cervix and the operator would allow the escape of air, deflating the vagina. Additionally, in both cases, the air alone may not have the strength to hold the vagina open as the vaginal walls can exert significant inward force, collapsing the field of view. Moreover, the noises and feeling of the inflation of a device inside the vagina, or air being pushed inside the vagina, may be uncomfortable for patients both physically and emotionally.

Still, there are drawbacks with the traditional two blade design. For one, tissue can enter between the blades once they are opened inside the vaginal cavity, a common occurrence that providers characterize as "side wall encroachment." Women, especially obese women, women with multiple vaginal births, or those with vaginal laxity, may have extra tissue in the side walls of the vagina that may fall into the space between the two blades once opened. This can cause problems for operators, particularly in providing clear visualization of the vagina and cervix, which potentially limits the effectiveness of the procedure. Furthermore, with all patients, when trying to close the speculum blades, tissue and/or pubic hair may become pinched between the blades. Pinching is extremely painful for patients and difficult for the operator to avoid without removing the speculum in an open position, which causes significant discomfort to the patients as well. There are no satisfactory solutions for these problems, resulting in tremendous patient discomfort with the entire speculum experience.

In an attempt to limit sidewall encroachment and allow for better visualization of the vaginal walls and cervix, operators may attempt to place condoms or portions of medical gloves over the speculum. This is an unsatisfactory and ineffective approach as condoms and gloves were not designed to support the internal pressure of the vaginal walls, but to be as thin as possible. Furthermore, using these solutions can result in both condoms and glove fingers, or torn portions of them, being left behind in the vaginal cavity following removal of the speculum. Alternatively, operators may choose to use larger speculums to provide a larger viewing/accessing window to compensate for tissue entering the side of the speculum between the blades. However, increasing the size of the speculum can provide discomfort to patients. Moreover, while there are now different sizes of speculums offered for an examination, it can be hard to determine the correct size for a patient as the size of the patient does not necessarily correlate with the size of the speculum that should be used.

An additional drawback to the traditional speculum design is that speculums are traditionally made of metal, though some made with disposable plastic have been increasing in use. When the speculum is made of metal, it can feel cold to the patient upon entry to the vaginal cavity, especially in comparison to the internal temperatures of the body, which can result in discomfort for the patient during the procedure. This may result in the patient tensing up and making the procedure more painful. Even when made of plastic, the design of the speculum is generally the same as the traditional design (but for some differences that may exist in the locking mechanisms, wall thicknesses, consistencies between the types of plastic, etc.), meaning that even plastic speculums may face some of the same drawbacks as traditional speculums.

Embodiments herein generally relate to accessories to improve speculum devices, components of the same, and methods of making and using the same. The devices and components overcome many drawbacks of existing speculum devices and/or they provide new improvements that have not been previously seen. For example, described herein according to some embodiments are speculum accessories or modifiers that minimize discomfort for the patient, while providing improved accessibility and visibility for the practitioner. In one aspect, a sleeve accessory is configured for positioning on a speculum, either on an existing speculum design or an updated speculum design, to cover an insertion portion of the speculum.

SUMMARY OF THE INVENTION

One embodiment relates to a sleeve accessory for use with a medical speculum. The sleeve accessory includes a cylindrical sleeve body comprising an outer surface, an inner surface, the inner surface defining a hollow sleeve channel, and at least one open end. The sleeve body is configured to receive an insertion portion of a medical speculum in the hollow sleeve channel, and the sleeve body is configured to expand from a first state to a second state.

Another embodiment relates to a kit. The kit includes a speculum, and the speculum includes a handle and an insertion portion, the insertion portion including an upper bill and a lower bill coupled to the handle. The kit also includes a sleeve accessory. The sleeve accessory includes a cylindrical sleeve body including an outer surface, an inner surface, the inner surface defining a hollow sleeve channel, and at least one open end. The sleeve body is configured to receive the insertion portion of the speculum in the hollow sleeve channel, and the sleeve body is configured to expand from a first state to a second state.

Another embodiment relates to a method of preparing a speculum for a medical procedure. The method includes providing a speculum having a pair of bills, and providing a sleeve accessory. The sleeve accessory includes a cylindrical sleeve body including an outer surface, an inner surface, the inner surface defining a hollow sleeve channel, and at least one open end. The sleeve body is configured to receive the pair of bills of the medical speculum in the hollow sleeve channel, and the sleeve body is configured to expand from a first state to a second state. The method further includes positioning the sleeve body over the pair of bills of the speculum.

Another embodiment relates to a method of performing a vaginal examination or medical procedure on a patient, comprising, providing a speculum device comprising a sleeve; inserting the speculum with the sleeve into the vagina of the patient; and performing the examination or medical procedure.

Another embodiment relates to a method of minimizing side wall encroachment or pinching in a vaginal examination or procedure, comprising, providing a speculum device comprising a sleeve according to one or more of the embodiments in the specification; inserting the speculum with the sleeve into the vagina of the patient such that side wall encroachment is minimized, reduced or avoided, or such that pinching of sidewall tissue is reduced, minimized or avoided during use of the speculum device for an examination or medical procedure.

DETAILED DESCRIPTION

Figure 1:
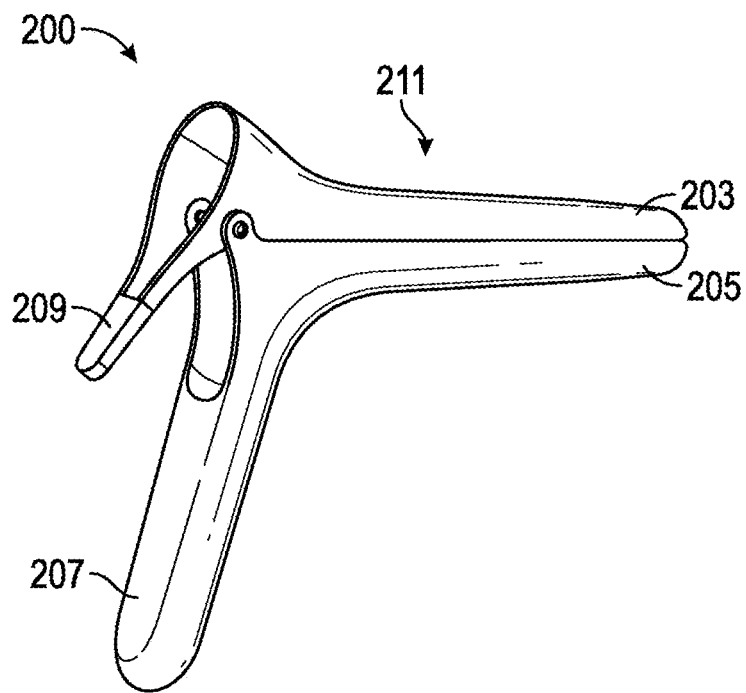
FIG. 1 is a side perspective view of a medical speculum on which a sleeve accessory according to various embodiments can be used.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented herein. It will be readily understood that the aspects of the present disclosure, as generally described herein and illustrated in the Figures, can be arranged, substituted, combined, and designed in a wide variety of different configurations, all of which are explicitly contemplated by and form part of this disclosure.

Referring to the figures generally, a sleeve accessory, or modifier sleeve, for a medical speculum is shown. The sleeve accessory may be used on any traditional speculum or any new or updated speculum design, including speculums that may be specifically designed for use with the sleeve accessory according to the present embodiments. The sleeve has an expandable body portion and is configured to be removably attached to an insertion portion of a speculum. In certain uses, a practitioner may be able to select a speculum with a narrower profile than the practitioner would regularly select because the sleeve reduces some of the previously described shortcomings of the traditional speculum design, for example, the problem of vaginal side wall tissue falling into the user's line of sight during use.

The devices described herein can provide any of a number of benefits. For example, using an outer delivery cartridge over the expandable sleeve to position the sleeve on the speculum can provide the benefit of a more sanitary procedure because the user can place a device comprising both the outer cartridge and the inner sleeve onto a speculum by contacting only the outer cartridge, which can maintain the cleanliness (e.g., sanitary or even sterility) of the inner sleeve. Alternatively, the sleeves may be packaged individually in order to maximize cleanliness. An inner gripping mechanism and/or ribbed details of the sleeve also can reduce slippage of the sleeve before, during, or after a procedure. Other advantages are apparent as well. The devices are described more fully herein.

Referring now to FIG. 1, a two-blade speculum is shown according to certain traditional designs. As shown, the speculum 200 has an upper bill 203 and a lower bill 205, a handle 207, and a lever 209. The upper bill 203 and the lower bill 205 together comprise an elongated insertion portion 211. The insertion portion 211, which is expandable as described herein, may be inserted into the vaginal cavity of a female patient. During insertion, the upper bill 103 and the lower bill 105 are in a closed position, wherein there is a minimal amount of space between the two bills. Once inserted and in order to dilate the vaginal cavity, the bills 203 and 205 are separated into an open position by pressing the lever 209 towards the handle 207. In accordance with typical speculum designs, the speculum 200 may be made of any sturdy biomaterial including metals and plastics.

Figure 2A:
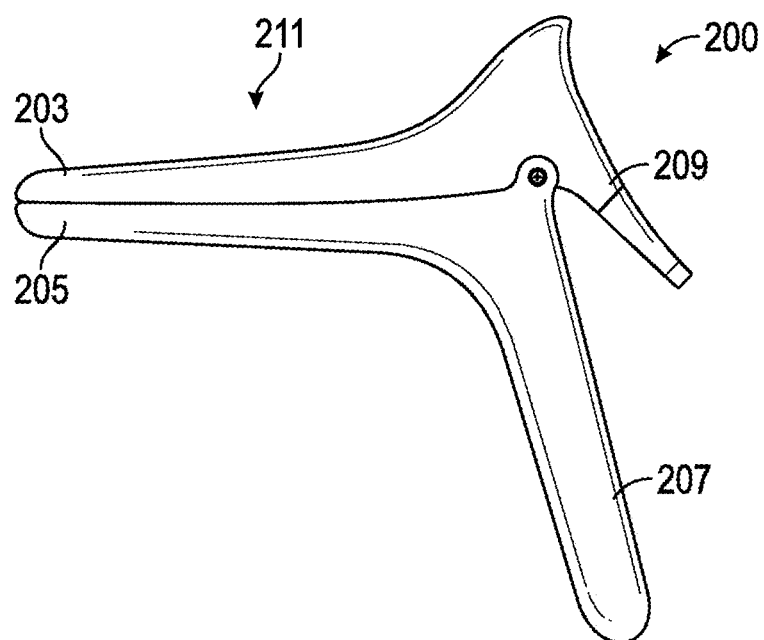
FIG. 2A is a side view of the medical speculum of FIG. 1.

Referring now to FIG. 2A, a side view of speculum 200 is shown. The upper bill 203 and the lower bill 205 may be configured in such a way that when in the closed position, the upper bill 203 and the lower bill 205 are wider near the handle 207 than near a body or end of the insertion portion 211, i.e., the bills 203 and 205 distend quickly to create somewhat of a cone shape near the handle 207, as shown in the side view of FIG. 2A. The bills 203 and 205 may maintain a constant shape after the cone, forming the elongated insertion portion 211. The upper bill 203 and the lower bill 205 of the elongated insertion portion 211 may have a uniform width or diameter as the bills 203 and 205 extend away from the handle 207. In other embodiments, the proximal portion of the bills 203 and 205 near the handle 207 may be up to two times wider than the distal end of the bills 203 and 205.

Figure 2B:
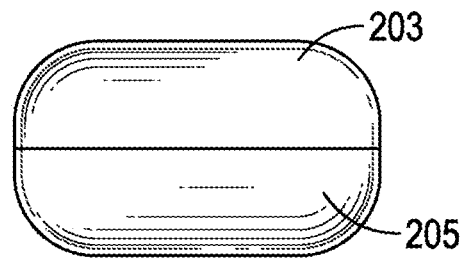
FIGS. 2B-2D are front views of the bills of the speculum of FIGS. 1 and 2A according to various embodiments.
Figure 2C:
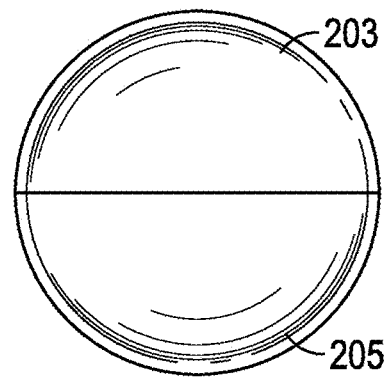
Figure 2D:
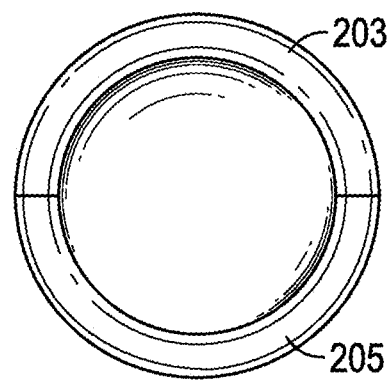

As illustrated in FIGS. 2B-2D, the bills 203 and 205 may be formed in various shapes. As seen in the front view of the bills 203 and 205 shown in FIG. 2B, the elongated insertion portion 211 may have a width that is larger than a height of the elongated insertion portion 211, creating an oblong shape when viewed from the front. Alternatively, in another embodiment, the bills 203 and 205 may each have a semi-circular cross section along the length of the bills 203 and 205 such that when the bills 203 and 205 are closed, a circular shape is formed when the bills 203 and 205 are viewed from the front, as seen in FIG. 2C. In yet another embodiment, the bills 203 and 205 may be "hollow' with outer inner edges that are circular such that when the bills 203 and 205 are in the closed position and viewed from the front, a cross section of the bills 203 and 205 is a ring shape, as seen in FIG. 2D. Beneficially, a ring-shaped cross section of bills 203 and 205 may provide a larger viewing opening for a user when the bills 203 and 205 are in the open position.

Referring back to FIG. 2A, at a distal end of the elongated insertion portion 211, away from the proximal handle 207, the bills 203 and 205 may be rounded (e.g., the bills 203 and 205 may each be rounded, the ends of bills 203 and 205 closed together may form a rounded end, etc.). A rounded end may provide more comfort to a patient while receiving the speculum 200 in a cavity. The bills 203 and 205 may also be configured such that when in the closed position, the end of each bill 203 and 205 do not abut one another, creating a gap which helps to prevent tissue from becoming lodged in between the bills 203 and 205. In one embodiment, the bills 203 and 205 may be of the same length such that when the bills 203 and 205 are closed, they form a smooth, continuous end to the insertion portion 211. Alternatively, in another embodiment, one of the bills 203 and 205 may be longer than the other, such that when the bills 203 and 205 are in the closed position, the longer bill juts out from beneath or above the other bill.

As shown in FIG. 2A, the handle 207 includes an upper portion and a lower portion. The upper portion of the handle 207 is coupled to bills 203 and 205. The lower portion provides a location for the user to hold the speculum 200. Coupled to the handle 207 is the lever 209. The lever 209 includes a mechanism for opening and closing bills 203 and 205. While the lever 209 is shown to be coupled to the upper portion of the handle 207, the lever 209 may be coupled to the handle 207 at any location. In some embodiments, the speculum 200 may also include a mechanism for locking the bills 203 and 205 into an open position. As an example, the user may press a button on the speculum once the user moves the bills 203 and 205 into a desired open position via the lever 209, the button locking the bills 203 and 205 into that open position. To close the bills 203 and 205, the user may press the button again, thereby deactivating the locking mechanism and allowing the user to move the bills 203 and 205 to the closed position via the lever 209. In this example, the button may be a toggle switch, where pressing one side of the toggle switch locks the bills and pressing the other side of the toggle switch releases, or unlocks, the bills. As another example, the bills 203 and 205 may automatically lock into the open position once the user moves the lever 209 past a certain "locking point." To unlock the bills 203 and 205, the user may move the lever 209 down past the locking point or, alternatively, up further past the locking point, at which point the locking mechanism may deactivate and the user may close the bills 203 and 205 by the lever 209.

Though specific reference is made in this specification to the elements or features of speculum 200, it is understood that the accessory or modifier elements described herein may be used with any speculum having an elongated and expandable insertion portion, such as any two blade speculum design. The features herein used to describe speculum 200 may also be present on any other speculum on which the accessory or modifier elements described herein may be used.

Figure 3:
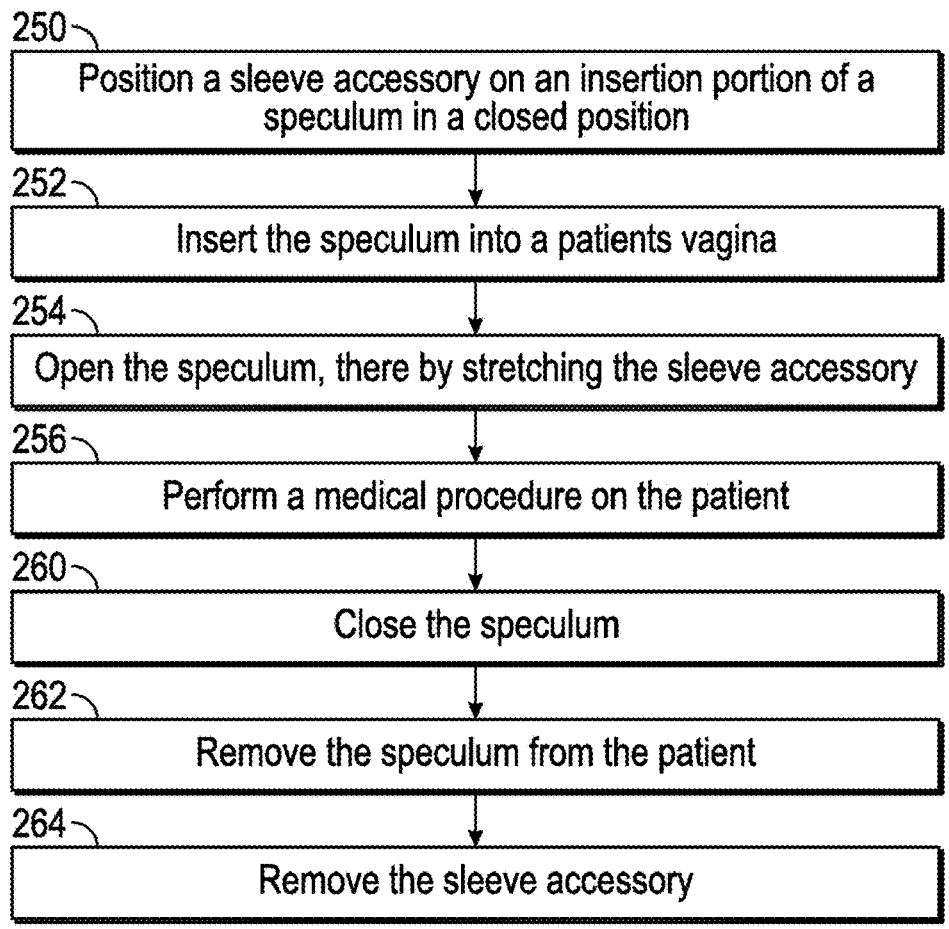
FIG. 3 is a flow diagram of a process of using a speculum with a sleeve accessory, according to one embodiment.

FIG. 3 shows a flow diagram illustrating a process for using a sleeve accessory with a speculum, such as speculum 200, according to one embodiment. At step 250, a user positions a sleeve accessory on an insertion portion of a speculum, such as insertion portion 211 on speculum 200, while the speculum is in a closed position. A sleeve accessory may include a cylindrical sleeve body with an opening whereby the user may roll, push, etc. the sleeve accessory onto the insertion portion of the speculum, such as insertion portion 211 of speculum 200. In some embodiments, the sleeve accessory may include a delivery cartridge or package to aid the user in positioning the sleeve accessory and/or to help the sleeve accessory remain sanitary during the positioning process.

At step 252, the user inserts the speculum with the attached sleeve accessory into a patient's vagina. At step 254, the user sets the speculum to the open position, thereby separating bills of the insertion portion and stretching the sleeve accessory. The user may open the speculum, for example, by applying a force to the lever 209 of speculum 200. When the speculum is opened, the bills 203 and 205 move away from each other, causing the sleeve positioned on the bills 203 and 205 to stretch. At step 256, the user performs a medical procedure on the patient by using the speculum in the open position. The medical procedure may be any obstetric or gynecological procedure, such as an examination of the vaginal cavity, a Pap smear, an insertion or removal of an intrauterine device (IUD), an insemination, a sexually transmitted infection (STI) testing, a tissue collection, a biopsy, or an electrosurgery.

After the user completes the medical procedure, the user closes the speculum, as shown at step 260. The user may do this, for example, by applying an opposite force to the lever 209 of speculum 200. Additionally, the user may need to deactivate a locking mechanism of the speculum that is keeping the bills of the speculum in an open position before the user may be able to close the speculum. At step 262, the user removes the speculum from the patient, and at step 264, the user removes the sleeve accessory from the speculum. The user may remove the sleeve accessory by performing the opposite of the action used to position the sleeve accessory on the speculum, e.g., rolling the sleeve accessory off, pushing the sleeve accessory off, etc. Alternatively, the user may use a removal device that helps the user remove the sleeve accessory from the insertion portion of the speculum.

Figure 4A:
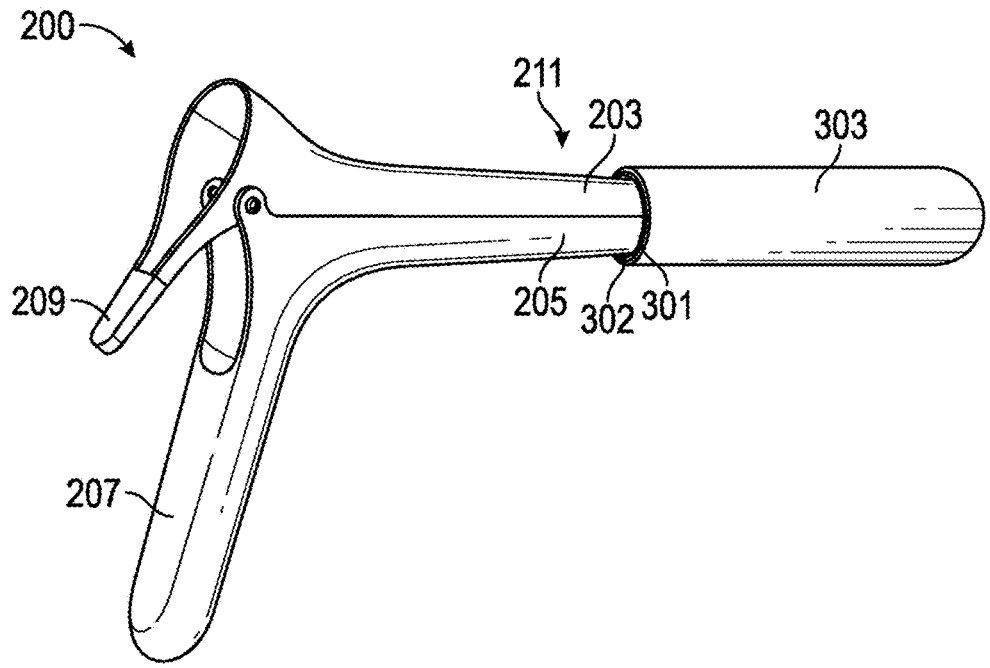
FIG. 4A is a side perspective view of an embodiment of a sleeve accessory being positioned on a medical speculum.

FIGS. 4A through 8 illustrate portions of the processes 250-264 described above. FIG. 4A depicts the positioning of a sleeve accessory 301 on the elongated insertion portion 211. As shown, the sleeve 301 is configured to be positioned on the elongated insertion portion 211, to surround or enclose both bills 203 and 205, while the bills are in a closed position. In some embodiments, the sleeve 301 has a cylindrical sleeve body. By "cylindrical" it is meant that the sleeve body has a continuous, longitudinal shape that surrounds a hollow area (i.e., a hollow sleeve channel) within an inner wall or surface of the cylinder. The cylindrical sleeve body is not limited to a circular cylinder and may instead have a cross-sectional shape that is a square, a rectangle, a circle, an oval, a triangle, and so on. In the embodiment shown, the sleeve 301 has a cylindrical shape with a proximal opening 302 through which the insertion portion 211 can be inserted. In the embodiment shown, the shape of the sleeve 301 substantially matches the shape of the bills, which may be in one of the shapes shown in FIGS. 2B-2D or may be in another shape, on which the sleeve 301 is being positioned. As such, the cylindrical body of the sleeve 301 may have a uniform width or diameter between a distal end of the sleeve body and a proximal end of the sleeve body while the sleeve 301 is in an un-stretched or unexpanded state, to match a uniform width or diameter of the bills 203 and 205 extending away from the handle 207. In one embodiment, the uniform diameter of the cylindrical body of the sleeve 301 may range between 0.25 inches and 3.0 inches. In other embodiments, the sleeve 301 may comprise a different natural shape than the shape of the bills 203 and 205, and may also have a non-uniform width or diameter ranging between 0.25 and 3.0 inches when in an un-stretched or unexpanded state.

FIG. 4A also depicts the positioning of the sleeve 301 being facilitated by a delivery cartridge 303 which contains the sleeve 301 therein. As shown, both the sleeve 301 and the delivery cartridge 303 are slid over the insertion portion 211 of the speculum 200 for positioning the sleeve thereon. As shown in FIG. 4A, the cartridge 303 may contain the full length of the sleeve 301. Alternatively, in another embodiment, the cartridge 303 may contain only a portion of the sleeve 301. The cartridge serves as an additional means of sanitation and comfort for the patient, as the patient knows that an outer portion of the sleeve 301 to be positioned in the patient's vagina has had limited, if any, contact with the hands of anyone handling the sleeve 301 or any other item which may transfer dirt, germs, or otherwise unsanitary elements to an outer surface of the sleeve 301.

Figure 4B:
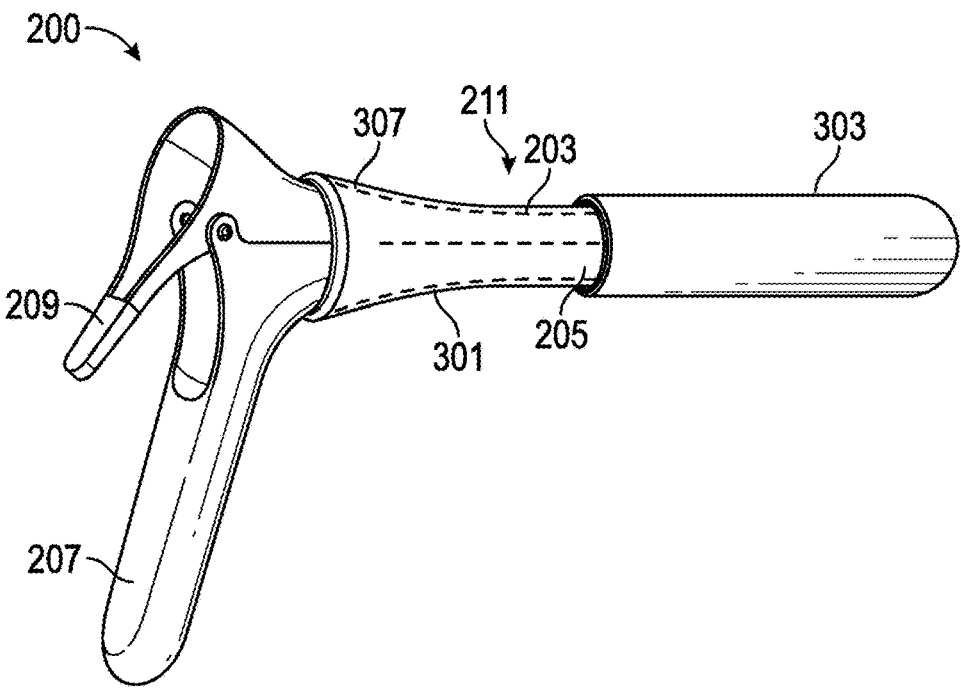
FIG. 4B is a side perspective view of the sleeve accessory of FIG. 4A positioned on a medical speculum during removal of a delivery cartridge.

As shown in FIG. 4B, once the sleeve 301 has been moved into the desired position on the speculum 200, the sleeve 301 is released from the cartridge 303, and the cartridge 303 may be removed. In some embodiments, the cartridge 303 includes a release mechanism which releases, ejects, disengages, or otherwise causes the separation of the sleeve 301 and the cartridge 303. In some embodiments, the cartridge 303 may contain one sleeve 301. In other embodiments, the cartridge 303 may contain multiple sleeves 301. The cartridge 303 may be disposable after it has delivered the sleeve 301. Alternatively, the cartridge 303 may be reusable, e.g., after re-sterilization.

In one embodiment, the sleeve 301 may be packaged and stored in the cartridge 303 until the sleeve 301 is to be used. In this embodiment, the cartridge 303 and the sleeve 301 stored in the cartridge may be packaged in an individual container, such that when the sleeve 301 is needed, the user selects the container, opens the container and removes the cartridge 303 containing the sleeve 301, positions the sleeve 301 on the insertion portion 211 of the speculum 200 by using the cartridge 303, and disposes the cartridge 303. Additionally, the cartridge and/or the container may be marked, colored, or otherwise indicated to show the size of the sleeve, which can make it easier for a practitioner to select a device sized appropriately for a patient. In another embodiment, each cartridge 303 may store, and be packaged with, a plurality of sleeves 301. In another embodiment, each sleeve 301 may be stored in an individual container designed to accommodate the shape of the sleeve 301. In this embodiment, when a sleeve 301 is needed, the user may select a container with a sleeve 301, open the container and remove the sleeve 301, and position the sleeve 301 on the speculum 200. Alternatively, the user may insert the sleeve 301 into a delivery cartridge 303, use the delivery cartridge 303 to position the sleeve 301 onto the insertion portion 211 of the speculum 200, and either dispose of the cartridge 303 or re-sterilize the cartridge 303 for another use. In still another embodiment, a container may store a plurality of sleeves 301 in individual compartments designed to accommodate the shapes of the sleeves 301.

The sleeve 301 may also be provided in a kit form with the delivery cartridge 303 and/or the speculum 200. In one embodiment, the kit may include one sleeve 301 and one speculum 200. In another embodiment, the kit may include a plurality of speculums 200 of varying lengths and widths and of varying expansion capabilities (i.e., capable of opening the bills 203 and 205 in different ways, to different opening lengths, etc.) and one or more sleeves 301 configured to fit the plurality of speculums 200. In another embodiment, the kit may include a plurality of sleeves 301 of varying lengths and widths and one or more speculums 200. In yet another embodiment, the kit may include one or more sleeves 301 of varying lengths and widths; one or more speculums 200 of varying lengths, widths, and expansion capabilities; and one or more delivery cartridges 303 configured to fit the one or more sleeves 301 and position the one or more sleeves 301 on the one or more speculums 200. In yet another embodiment, the kit may further include accessories related to the needs of the examination or the procedure, for example, an IUD insertion device, a disposable electrosurgery tool, etc. In yet another embodiment, a plurality of sleeve accessories can be provided loosely in a large package or box.

The sleeve 301 may be made of one or more compliant or partially compliant materials, such as latex, vinyl, natural and synthetic rubbers, silicone, nylon, polyethylene, polyurethane, polypropylene, and non-degradable or degradable elastomers. In preferred embodiments, the sleeve 301 may be made of a polyisoprene (PI), a polyurethane (PU), a thermoplastic polyurethane (TPU), a styrene copolymer (SBS), and/or a thermoplastic elastomer (TPE). The material of the sleeve 301 may range from completely transparent to translucent or frosty to opaque. Alternatively, the sleeve 301 may include a finish that ranges from completely transparent to translucent or frosty to opaque. Different finishes may be used for different types of gynecological examinations or procedures. For example, a thicker and/or more opaque sleeve may be used for a surgical procedure, such as an electrosurgery, while a thinner and/or more clear sleeve may be used for a gynecological examination or procedure. The cartridge 303 may be made of similar materials, or it may be made of another material such as paperboard, corrugated fiberboard, polycarbonate and other plastics, and other less complaint materials.

The sleeve 301 or a portion of the sleeve 301 may optionally be coated with one or more bioactive or therapeutic agents, lubricants, or surface finishes. Examples of suitable bioactive or therapeutic agents include, but are not limited to, hormonal and non-hormonal contraceptive agents, cancer screening agents, vaginal spermicides, vaginal microbicides, antibacterial agents, antifungal agents, antiviral agents, anti-HIV agents, and cancer treatment agents, or combinations thereof. The bioactive or therapeutic agents may be in any suitable formulation that may be applied to the surface of a vaginal speculum, such as a liquid, gel and powder.

In some embodiments, lubricants may be applied to at least a portion of an inner surface of the sleeve 301 and/or to an outer surface of the sleeve 301. When applied to the inner surface of the sleeve 301, the lubricant may, e.g., aid in positioning the sleeve 301 on the insertion portion 211. When applied to an outer surface of the sleeve, the lubricant may, e.g., help the speculum 200 with the attached sleeve 301 be more easily inserted into the patient. In other embodiments, the lubricant on the interior surface and/or exterior surface of the sleeve 301 may instead be, or may be combined with, a powder applied to the sleeve 301 or a surface texture finished into a material of the sleeve 301. The powder and/or surface texture may likewise, e.g., aid the user in positioning the sleeve 301 on the insertion portion 211, help the speculum 200 with the attached sleeve 301 be more easily inserted into the patient, and so on. In various embodiments, the sleeve 301 may come with lubricant and/or powder pre-applied, the sleeve 301 may come in a kit with lubricant and/or powder included for the user to apply to the sleeve 301, the sleeve 301 may come with instructions that recommend types or brands of lubricants and/or powders for the user to apply to create the beneficial effects discussed above, etc.

Figure 4C:
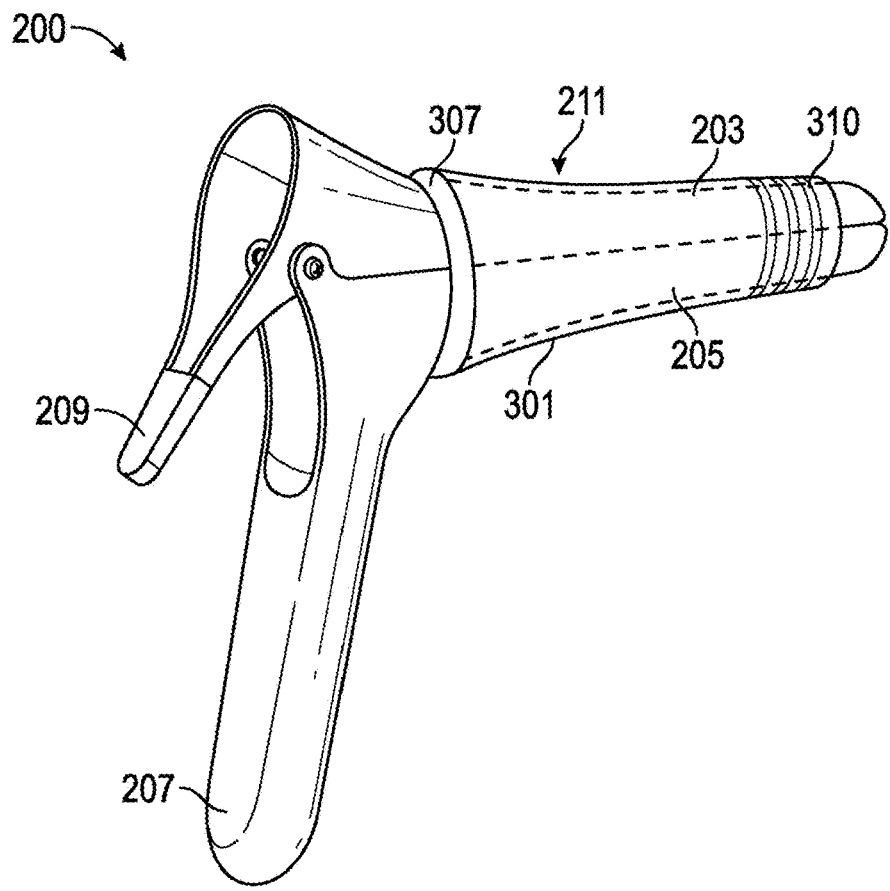
FIG. 4C is a side perspective view of the sleeve accessory of FIG. 4A positioned on a medical speculum after removal of a delivery cartridge.

The sleeve 301 may, additionally or alternatively, include ribbed details 310 that help the sleeve 301 remain securely fastened onto the insertion portion 211. In one embodiment, the ribbed details may be limited to a portion of the sleeve 301 secured to the smaller, narrower, distal end of the insertion portion 211, as shown in FIG. 4C. In other embodiments, the ribbed details may, additionally or alternatively, be limited to a portion of the sleeve 301 secured to the larger, proximal end of the insertion portion 211 near the handle 207, or be distributed throughout the length of the sleeve 301. In some embodiments, the ribbed details may instead be, or may be combined with, texture differences provided on an inner surface of the sleeve 301 and/or gripping elements positioned on an inner surface of the sleeve 301 (e.g., such as flanges 605 included in sleeve 601 shown in FIGS. 6A and 6B), that may help the sleeve 301 remain securely fastened onto the insertion portion 211.

The proximal opening of the sleeve 301, as well as a distal opening included in some embodiments of the sleeve 301, may have a ridged finish, shown as end ring 307 in FIG. 4B. The ridged finish may be provided to give the user a ridge to aid the user in positioning the sleeve 301 on the insertion portion 211, to finish the end of the sleeve 301 so that the end of the sleeve 301 is less easily ripped or otherwise damaged, to provide additional tension to adhere the sleeve 301 to the insertion portion 211, and so on. As shown in FIGS. 4B and 4C, the ridged finish may be provided as an end ring 307, which may be a rolled bead edge (i.e., similar to a condom) or may be formed from an encapsulated ring (i.e., a ring that is rolled into the end of the sleeve 301 and cured). In other embodiments, the ridged finish may be provided as a dip in the material of the sleeve 301, a secondary dip in another polymer material (e.g., of a different thickness, durometer, color, etc.) attached to the sleeve 301, an otherwise attached or adhered secondary material that finishes the opening(s), and so on.

Figure 5A:
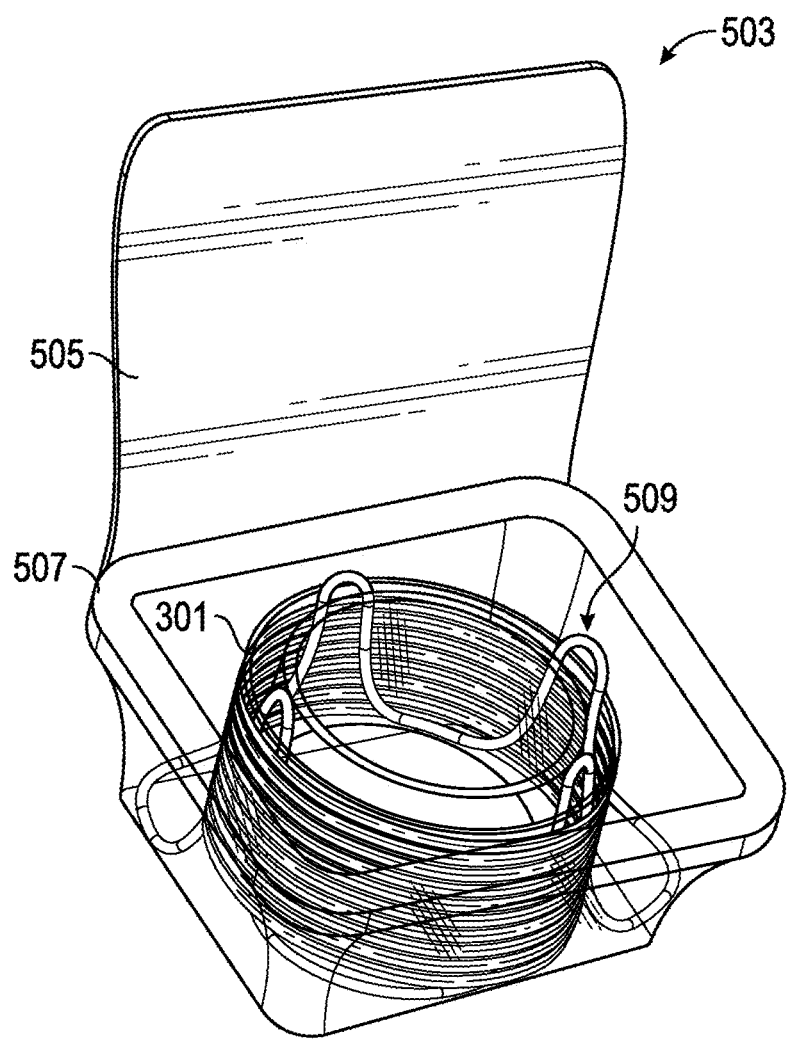
FIG. 5A is a perspective view of a cartridge for storing and positioning a sleeve accessory on a speculum.
Figure 5B:
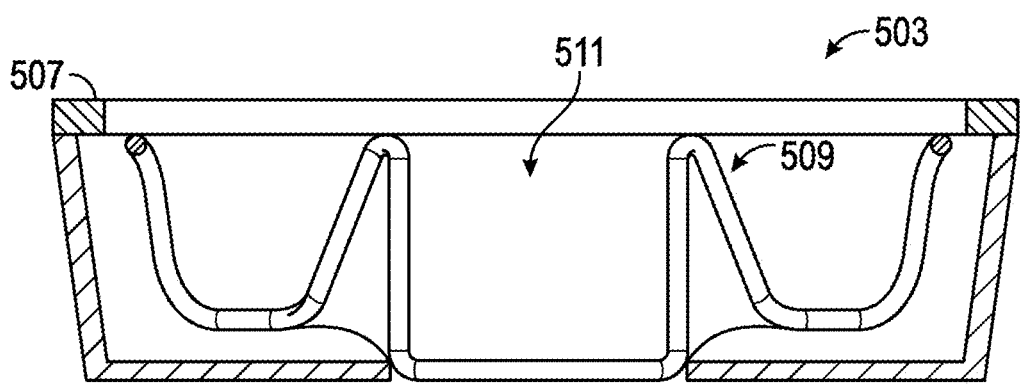
FIG. 5B is a cross-sectional view of the cartridge of FIG. 5A.

FIGS. 5A-5B depict an alternative embodiment of a cartridge 503 that can be used to transport, store and/or position on a speculum a sleeve accessory according to any of the exemplary embodiments disclosed herein. As shown in FIG. 5A, the sleeve accessory can be held in the cartridge 503 in a compressed form in which the cylindrical body of the sleeve 301 is bunched, pressed, coiled, etc. together such that the sleeve is compressed down to a smaller size. A cover, such as film 505, can be removably secured to a top edge 507 of the cartridge 503. When the sleeve is to be used, the film 505 is peeled away from the top edge 507, thereby exposing the sleeve in the cartridge. The cartridge bottom may define a central post 509 around which the sleeve is positioned. In some embodiments, the central post 509 is hollow and defines a cavity 511. The cavity 511 provides a space for the practitioner to insert the distal end of the speculum and pull, or otherwise position, the sleeve around the bills of the speculum.

Figure 6A:
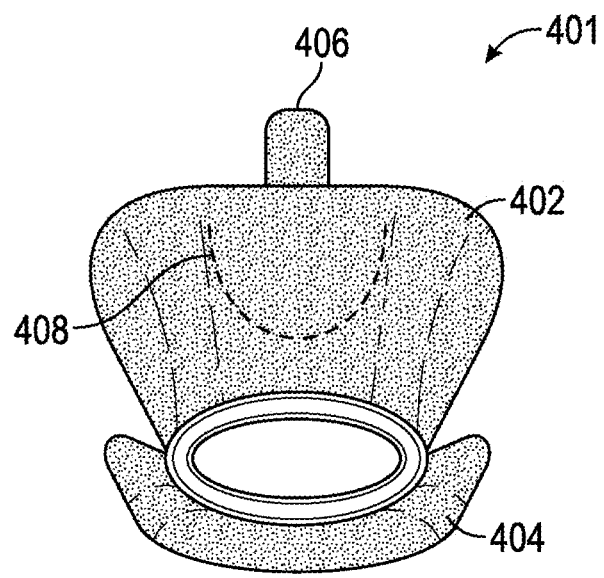
FIG. 6A is a front view of a second embodiment of a sleeve accessory.
Figure 6B:
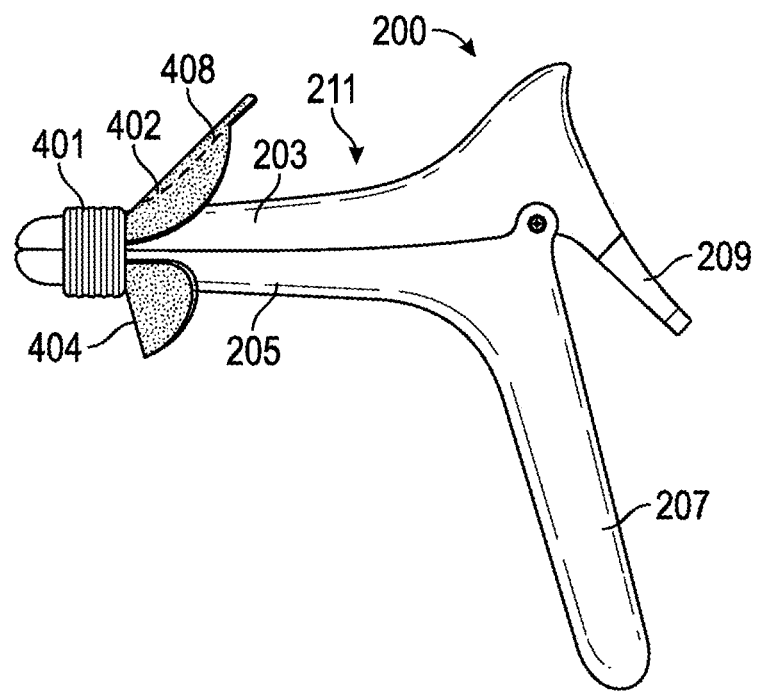
FIG. 6B is a side view of the sleeve accessory of FIG. 6A being positioned on a medical speculum.

Referring now to FIGS. 6A-6D, another embodiment of a sleeve accessory for a speculum is shown as sleeve 401. FIG. 6A illustrates a front view of sleeve 401. As shown in the front view of FIG. 6A, sleeve 401 has an oblong-shaped cross section. Further, as shown in FIGS. 6A and 6B, sleeve 401 includes openings at both ends of a cylindrical body of the sleeve 401 (i.e., at the proximal sleeve body end and the distal sleeve body end of the sleeve 401). However, in other embodiments, sleeve 401 may have a cross section in another shape (e.g., square, rectangle, circle, triangle, etc.) and/or may include an opening at only one end of the sleeve 401 (e.g., at the proximal end of the sleeve 401, similar to sleeve 301 shown in FIGS. 4A and 4B). Sleeve 401 also includes petals 402 and 404, as well as pull tab 406, positioned on the proximal end of the sleeve 401. The petals 402 and 404 may, for example, assist with positioning the sleeve 401 on the speculum and/or help the sleeve 401 conform and fit more closely to the speculum 200 once positioned on the speculum. In the embodiment of FIG. 6A, the petal 402 further includes a perforated edge 408 on the body of the petal 402. The body of the sleeve 401 may be made of any of the materials described above with respect to sleeve 301. The petals 402 and 404 and the pull tab 406 may be made of the same material(s) as the body of the sleeve 401, or the petals 402 and 404 may be made of one or more different materials from the sleeve 401.

Figure 6C:
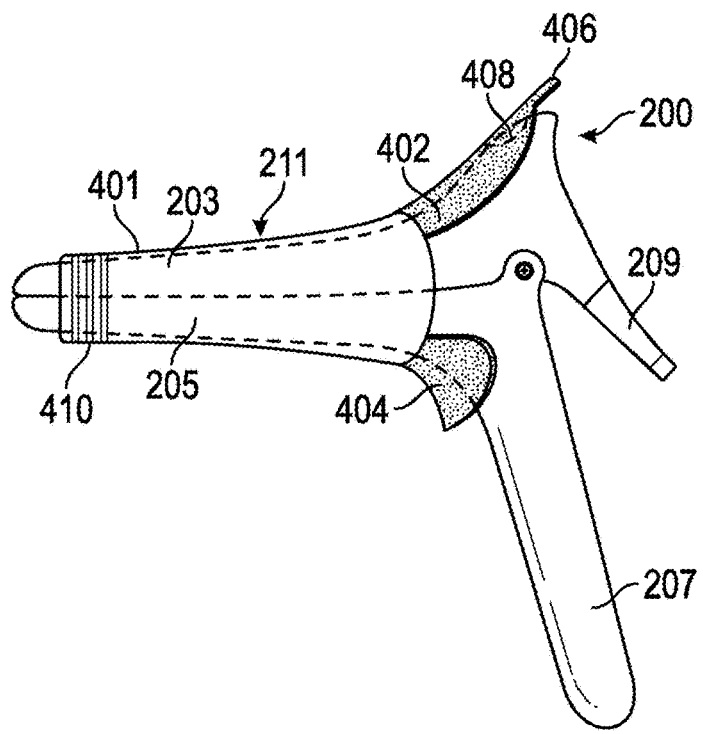
FIG. 6C is a side view of the sleeve accessory of FIGS. 6A and 6B on a medical speculum.

As shown in FIG. 6A and FIG. 6B, the sleeve 401 may be packaged in a compressed form in which the cylindrical body of the sleeve 401 is bunched, pressed, coiled, etc. together such that the sleeve 401 is compressed down to a smaller size. To be positioned on the speculum 200, the compressed sleeve 401 may be inserted onto the insertion portion 211 of the speculum 200 by the openings in the sleeve body, as shown in FIG. 6B, and stretched out across the insertion portion 211, as shown in FIG. 6C. A user may accomplish the positioning of the compressed sleeve 401 by, e.g., pulling the sleeve 401 across the insertion portion 211 by the pull tab 406 or the petals 402 and 404.

In one embodiment, the sleeve 401 may also, or alternatively, be positioned on the insertion portion 211 through a delivery cartridge, and may further be stored or packaged in the delivery cartridge. In another embodiment, the delivery cartridge may be configured to store and/or position a plurality of compressed sleeves 401. In yet another embodiment, sleeves 401 may be packaged into individual packaging containers designed to accommodate the compressed form of sleeve 401. In still another embodiment, sleeves 401 may be packaged in packaging containers designed to hold a plurality of compressed sleeves 401. The packaging containers may include individual compartments for each compressed sleeve 401, each compartment designed to accommodate the compressed form of a sleeve 401.

As shown in FIG. 6C, sleeve 401 includes ribbed details 410 on the distal end of the sleeve 401. The ribbed details 410 help the sleeve 401 remain securely fastened onto the insertion portion 211. In other embodiments, sleeve 401 may include ribbed details, additionally or alternatively, on the proximal end of the sleeve 401 or distributed along the length of the sleeve 401. In yet other embodiments, the sleeve 401 may, additionally or alternatively, include texture differences and/or gripping elements (e.g., similar to gripping elements 605 from sleeve 601 shown in FIGS. 6A and 6B) on an inner surface of the sleeve 401 to help the sleeve 401 remain securely fastened onto the insertion portion 211. Additionally, the sleeve 401 may include lubricants, powders, and/or surface textures applied to an inner surface and/or an outer surface of the sleeve 401, as described above with respect to sleeve 301. These lubricants, powders, and/or surface textures may work, for example, to help the sleeve 401 more easily slide onto the insertion portion 211 of the speculum 200 and/or, once the sleeve 401 is positioned on the speculum 200, help the speculum 200 be more easily inserted into a patient. The sleeve 401 may further include a ridged finish (e.g., similar to the end ring 307 of sleeve 301 shown in FIGS. 4A and 4B), as described above with respect to sleeve 301.

Figure 6D:
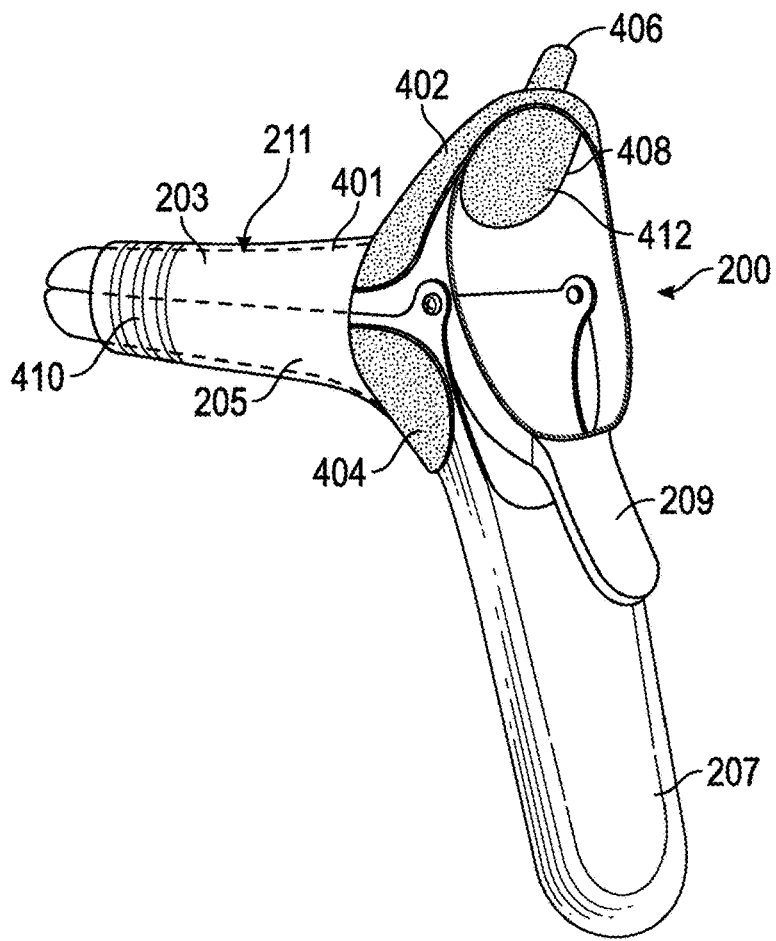
FIG. 6D is a rear perspective view of the sleeve accessory of FIGS. 6A-6C on a medical speculum.

Referring now to FIG. 6D, once the compressed sleeve 401 is inserted and positioned onto the insertion portion 211, the user may break the perforated edge 408, thereby forming a perforated pocket 412. The user may then tuck the perforated pocket 412 over a top edge of the top bill 203, as shown in FIG. 6D, to secure the sleeve 401 onto the speculum 200. In other embodiments, the perforated edge 408 may be located elsewhere on the sleeve 401 (i.e., not on the petal 402). Alternatively, instead of a perforated edge 408 used to create a perforated pocket 412, the sleeve 401 may include a pocket preformed into the petal 402 (e.g., the petal 402 may include a flap of material formed in the shape of a pocket) or elsewhere on the sleeve 401, such that the user may tuck the preformed pocket over the top edge of the top bill 203 to secure the sleeve 401 onto the speculum 200. In still other embodiments, the sleeve 401 may include another means of securing the sleeve 401 to the speculum 200, such as straps to wrap or fasten around a back of the speculum 200, an adhesive strip on the petal 402 and/or the petal 404 that sticks to the upper bill 203 and/or the lower bill 205, and so on.

Figure 7A:
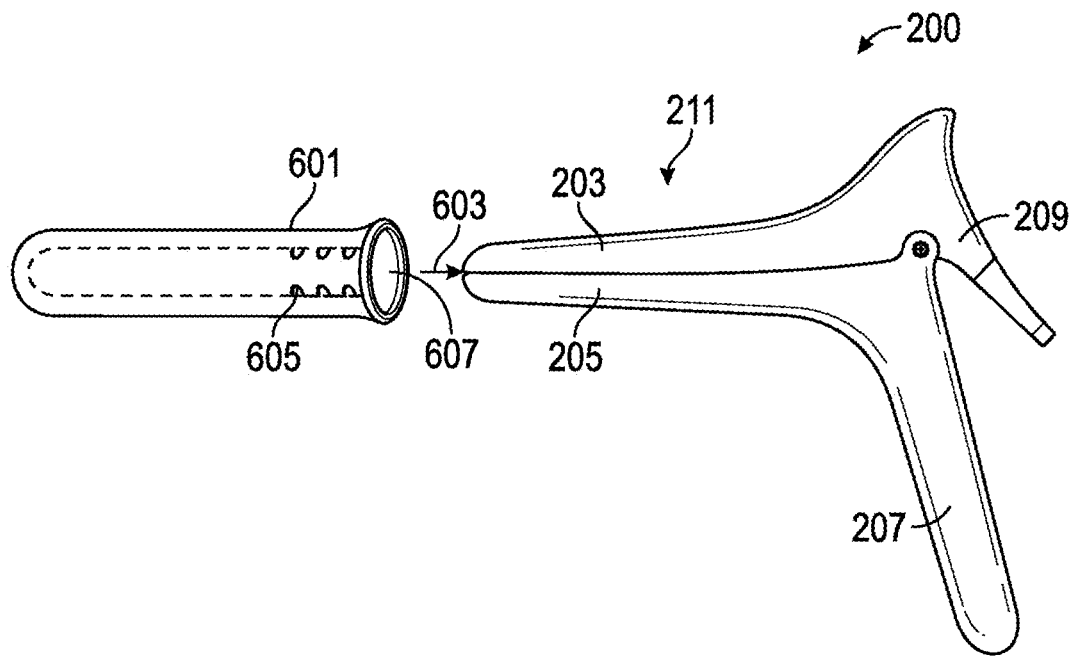
FIG. 7A is a side view of a sleeve accessory and a medical speculum depicting relative movement between the sleeve accessory and the medical speculum for positioning the sleeve on the speculum.
Figure 7B:
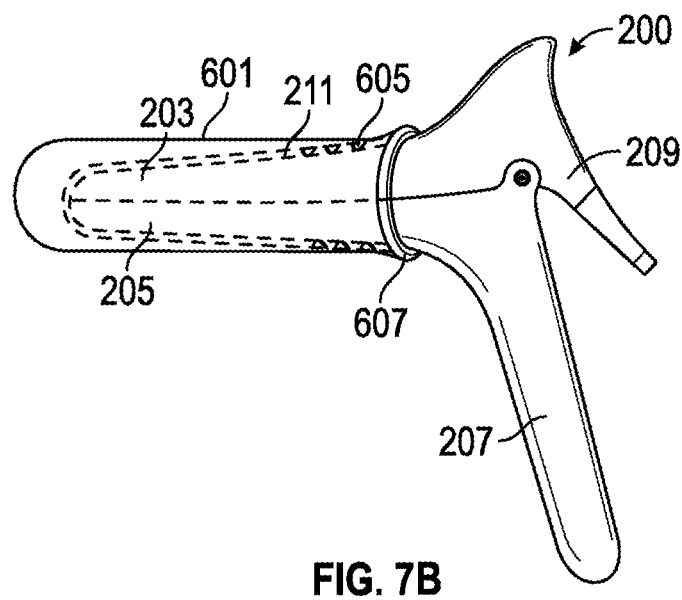
FIG. 7B is a side view of the sleeve accessory of FIG. 7A positioned on a medical speculum.

FIGS. 7A and 7B illustrate another embodiment of a sleeve accessory for a medical speculum, shown as sleeve 601. Sleeve 601 is designed similarly to sleeves 301 and 401, with a cylindrical sleeve body configured to be slid over an insertion portion of a speculum, such as insertion portion 211 of speculum 200. As shown in FIG. 7A, the sleeve 601 may be positioned onto the insertion portion 211 of the speculum 200 following an insertion path shown by arrow 603. In some embodiments, sleeve 601 may be positioned onto the insertion portion 211 using a delivery cartridge, such as delivery cartridge 303 shown in FIGS. 4A and 4B. As shown in FIGS. 7A and 7B, the cylindrical body of sleeve 601 has an open proximal end and a closed distal end. The sleeve 601 may further include a small hole or aperture (not shown) in the closed, distal end of the sleeve 601, which may allow for visualization, tissue sampling, etc. through the otherwise closed distal end. In other embodiments, sleeve 601 may have an open proximal end and an open distal end, similar to sleeve 401 shown in FIGS. 6A-6D.

As shown in FIG. 7B, once positioned on the insertion portion 211, the sleeve 601 surrounds the bills 203 and 205 and preferably has a snug fit around bills 203 and 205. As such, the sleeve 601 should not move along the bills 203 or 205 during insertion into the vagina or during a medical examination, procedure, or surgery being conducted on the vaginal or surrounding tissues.

In the embodiment shown in FIG. 7B, the sleeve 601 wraps around the distal end of the bills 203 and 205 so as to enclose the top portion of the bills 203 and 205, or extend up to the distal end of the bills 203 and 205. However, in other embodiments, the sleeve 601 may not reach the end of the bills 203 and 205 when the sleeve 601 is positioned on the bills 203 and 205 and instead have an open end (e.g., similar to sleeve 301 shown in FIG. 4C, similar to sleeve 401 shown in FIGS. 6C and 6D, similar to sleeve 700 shown in FIG. 8, etc.). In some embodiments, the sleeve 601 is positioned and dimensioned to cover at least 80% of the total length of the insertion portion 211. In other embodiments, the sleeve 601 is positioned and dimensioned to cover at least 50% of the total length of the insertion portion 211. In some embodiments, the sleeve 601 extends from the proximal end of the bills 203 and 205 towards the distal end, but does not reach the distal end of the bills 203 and 205 (e.g., similar to sleeve 301 shown in FIG. 4C, similar to sleeve 401 shown in FIGS. 6C and 6D, similar to sleeve 700 shown in FIG. 7, etc.). In other embodiments, the sleeve 601 may extend from the distal end of the bills 203 and 205 towards the proximal end but not reach the proximal end of the bills 203 and 205.

In order to prevent the sleeve 601 from sliding off the bills 203 and 205 during insertion, use, and/or removal of the speculum 200, the sleeve 601 may include gripping elements, such as ridges, bumps, flanges, indentations, etc., on the interior of the sleeve 601 to increase the resistance between the sleeve 601 and the bills 203 and 205. In FIGS. 7A and 7B, the gripping elements are in the form of flanges 605 extending inwardly from the interior of sleeve 601. The flanges 605 may alternatively extend substantially perpendicular to the longitudinal axis of the sleeve 601, may extend at an angle, or may extend at a combination of angles. In a preferred embodiment, as shown in FIGS. 7A and 7B, the flanges 605 extend at an angle towards the distal end of the sleeve 601 and bills 203 and 205. In this way, the flanges 605 are oriented in opposition to the direction of removal of the sleeve 601 from the speculum 200. Accordingly, small forces such as those that may act on the sleeve 601 during insertion, use, or removal are likely not strong enough to overcome the resistance created by the flanges 605. Other connection mechanisms for securing the sleeve 601 to the speculum 200 are intended to fall within the spirit and scope of the present disclosure, such as ribbed details and texture differences similar to those discussed above with respect to sleeves 301 and 401. The flanges 605 or any other connection mechanisms could also be used in any of the sleeves described herein, such as sleeve 301 of FIGS. 4A-4C, sleeve 401 of FIGS. 6A-6D, and sleeve 700 of FIG. 8.

Additionally, as shown in FIGS. 7A and 7B, the open proximal end of sleeve 601 includes a ridged finish in the form of an end ring 607. Similar to the end ring 307 discussed above with respect to FIG. 4B, the end ring 607 may provide a ridge to aid the user in positioning the sleeve 601 on the insertion portion 211, finish the end of the sleeve 601 so that the end of the sleeve 601 is less easily ripped or otherwise damaged, provide additional tension to adhere the sleeve 601 to the insertion portion 211, etc. In various embodiments, the end ring 607 may be provided as a rolled bead edge, formed from an encapsulated ring that is cured, provided as a dip in the material of the sleeve 601, provided as a secondary dip in another polymer material attached to the sleeve 601, etc. Additionally, in embodiments of sleeve 601 with more than one opening on the cylindrical body of the sleeve 601, each opening may include an end ring 607 (e.g., as illustrated by end rings 707 on sleeve 701 shown in FIG. 8). Moreover, similar to sleeves 301 and 401, the sleeve 601 may include lubricants, powders, surface textures, and so on to aid the sleeve 601 in being inserted onto the insertion portion 211 and/or to aid the speculum 200 in being inserted into a patient. Sleeve 601 may be made of any of the materials described above with respect to sleeve 301.

Once a sleeve accessory is inserted onto a speculum, the speculum may be used to carry out a medical procedure on a patient. The medical procedure may be any gynecological examination or procedure, such an examination of the vaginal cavity, a pelvic examination, a Pap smear, an insertion or removal of an IUD, an insemination, an STI testing, a tissue collection, a biopsy, or an electrosurgery. In the embodiment of FIGS. 7A and 7B, when the bills 203 and 205 are in the closed position seen in FIG. 7B, the speculum 200 can be inserted a patient's vagina. To do this, the user places the insertion portion 211 in line with an opening of the vagina and applies a force parallel to the bills 203 and 205 to push the bills into the vagina. The sleeve 601 may be made of a material that reduces the resistance between the vagina and the bills 203 and 205 of the speculum 200 during entry to and/or removal from the vagina. Alternatively, or additionally, the sleeve 301 may be covered in a lubrication, a powder, a surface texture, etc. to facilitate entry and removal of the bills 203 and 205 of the speculum 200. The sleeve 601 may come with lubrication and/or powder pre-applied, or the user may have to apply the lubrication and/or powder herself. The sleeve 601 may also come with a number of potential bioactive or therapeutic agents pre-applied.

The user may position the speculum 200 at a depth of the vagina to provide a clear view of the cervix when the bills 203 and 205 of the speculum are opened. As an example, the speculum 200 may be inserted so that the ends of the bills 203 and 205 are located below the cervix. Once the bills 203 and 205 are separated, the cervix may then be seen through the viewing opening created by the separation of the bills 203 and 205.

Figure 8:
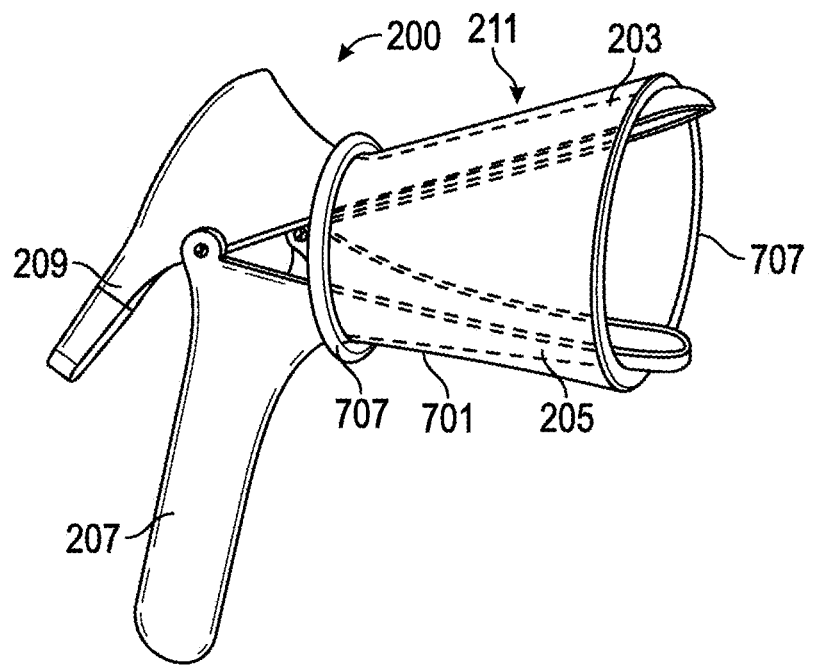
FIG. 8 is a side perspective view of a sleeve accessory positioned on a medical speculum in an open position.

FIG. 8 illustrates a sleeve accessory, shown as sleeve 700, positioned on a speculum, shown as speculum 200. Sleeve 701 is configured similarly to sleeves 301, 401, and 601 discussed above. As shown in FIG. 8, once the bills 203 and 205 are inserted into the vagina, the user then manipulates the lever 209 to separate and open the bills 203 and 205 and expand the sleeve 701. The bills 203 and 205 open, for example, when a force is applied to the lever 209. When force is applied to the lever 209, the opening between the bills 203 and 205 created by the separation of the bills 203 and 205 may be caused by both bills 203 and 205 moving, or either bill 203 or bill 205 moving. For example, the force applied on the actuation lever 209 may cause bill 203 to move, while bill 205 remains stationary. Bill 203 and/or bill 205 may be coupled to the upper portion of handle 207 by a hinge such that a force on actuation lever 209 causes a rotational movement of bill 203 and/or bill 205 about the hinge, separating the ends of bills 203 and 205. In one embodiment of the speculum 200, the user may need to apply the force throughout the procedure in order to keep the bills 203 and 205 in the open position. In another embodiment of the speculum 200, the speculum 200 may contain a locking mechanism whereby the user may lock the bills 203 and 205 into the open position.

When a force is applied to the lever 209 and the bills 203 and 205 of the speculum 200 separate, the sleeve 701 expands from a first state to a second state (i.e., from an unexpanded state to an expanded state). When the bills 203 and 205 separate, the sleeve 701 may stretch to accommodate the increase in distance between bills 203 and 205. Beneficially, the expansion of the sleeve 701 provides side wall retention for tissue encroachment from the side walls of the vagina, allowing the user to maintain an uninterrupted view of the vaginal cavity and cervix while viewing the vaginal cavity and cervix through the speculum 200. The expansion of the sleeve 701 also works to prevent vaginal tissue or pubic hair from entering the opening between the bills 203 and 205, as the bills 203 and 205 may cause pinching of the tissue or pubic hair that is painful for the patient when the bills 203 and 205 are returned to the closed position at the conclusion of the procedure, examination, or surgery.

Once the user has completed the procedure (e.g., inspection of the vaginal cavity and cervix, a Pap smear, an electrosurgery, etc.), the bills 203 and 205 should be returned to the closed position to remove the speculum 200 from the patient. To return the bills 203 and 205 to the closed position, the user may release the force from the lever 209. Removing the force, by itself, works to close the bills 203 and 205 for configurations of the speculum 200 where force needs to be applied to the lever 209 for the length of the procedure to maintain the viewing opening. However, for configurations of the speculum 200 where the lever 209 locks into place when the force is applied, a second force may also need to be applied to the lever 209 to overcome the locking mechanism and close the bills 203 and 205. The force may be applied in a direction opposite of the opening force. Alternatively, the lever 209 may be released by applying a second force in the same direction as the opening force to the lever 209 to move the lever 209 past the locking position, thereby releasing the lock and closing the bills 203 and 205. In configurations utilizing a toggle switch, the bills can be unlocked and closed by pressing the appropriate portion of the toggle switch. By returning the bills 203 and 205 to the closed position, the sleeve (e.g., sleeve 301, 401, 601, or 701) returns from the second position to the first position (i.e., from the expanded state to the unexpanded state).

Once the bills 203 and 205 of the speculum 200 are closed, the speculum 200 carrying the sleeve accessory, such as sleeve 301, 401, 601, and/or 701, can be removed from the patient. The speculum 200 may then be pulled along an axis parallel to the length of bills 203 and 205 to easily remove the speculum 200 from the patient.

Figure 9:
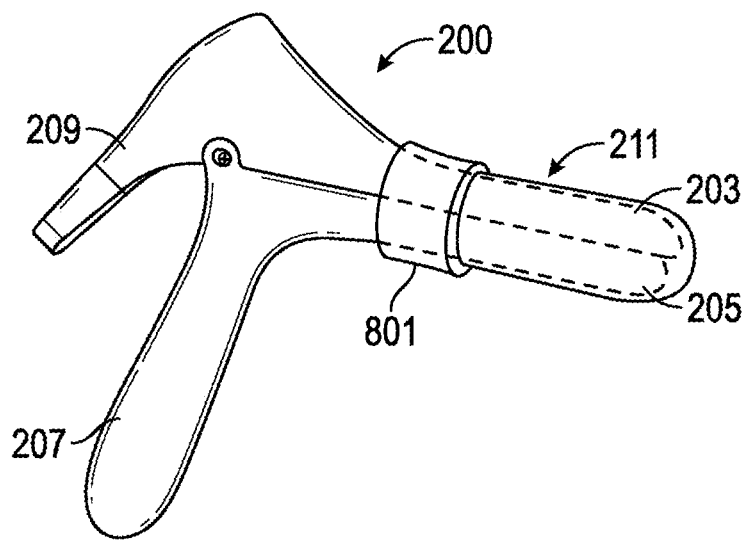
FIG. 9 is a perspective view of a sleeve accessory and a medical speculum during removal of the sleeve accessory from the speculum.

As depicted by FIG. 9, a sleeve accessory is removed from the speculum after use. FIG. 9 illustrates a used sleeve accessory, shown as sleeve 801, being peeled from the proximal end of the bills 203 and 205 to remove the sleeve 801 from the insertion portion 211. In some embodiments, the sleeve 801 may be removed by using a removal device that aids the user in sliding the sleeve off of the insertion portion 211. After removal, the sleeve accessory 801, if designed to be disposable, can be thrown away. In this way, the speculum 200 may remain relatively clean during a medical procedure, examination, or surgery and can undergo a quicker and less intensive sterilization because the tissue-contacting sleeve 801 is discarded after use and the device otherwise remains relatively free of contact with the patient tissue. Alternatively, the sleeve 801 may be able to be sterilized for reuse. Sterilizing the sleeve 801 may be more efficient and effective than sterilization of an unprotected speculum 200 after each use. Any of the sleeve accessories disclosed herein may be removed in the same way as sleeve 801.

The sleeve accessory, such as sleeves 301, 401, 601, 701, and 801 described herein, overcomes the previously described shortcomings of the traditional speculum in a variety of ways. First, the sleeve may be made of a rubber or other soft material that is warmer than the traditional metal speculum bills. As such, inserting a speculum with a sleeve accessory attached may be less shocking, and thus more comfortable, to a patient than a bare metal speculum. The material may be at least substantially transparent to allow for good visualization of the vaginal cavity through the speculum with attached sleeve. Furthermore, a slimmer profile speculum can be utilized because of the sleeve (e.g., because the sleeve allows for improved visualization such that a larger speculum is not necessary), which provides better comfort for the patient during the procedure, examination, or surgery involving the speculum. The sleeve moreover allows the speculum to be removed in a closed position while preventing the pinching of either tissues or pubic hair during the process, significantly improving patient comfort while reducing patient anxiety. Importantly, the sleeve also provides the side wall support between the upper bill and the lower bill of the speculum that allows the practitioner better and less impeded visualization into the vagina and cervix. When used during an electrosurgery, the sleeve accessory may additionally provide insulation to protect the vaginal walls of a patient during the electrosurgery procedure.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

The devices, components, methods and systems described herein can be combined with one or more of the devices, components, methods and systems described in any of U.S. Patent Application entitled "Speculum with Secondary Bills," filed on Dec. 28, 2016 and identified by U.S. Patent Application entitled "Insertable Sleeve for Speculum and Use Thereof," filed on Dec. 28, 2016 and identified by and U.S. Patent Application entitled "Ergonomically Designed Vaginal Speculum," filed on Dec. 28, 2016 and identified by each of which is incorporated herein by reference in its entirety.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A sleeve accessory for use with a medical speculum, comprising:
    a cylindrical sleeve body having a distal end and a proximal end and comprising an outer surface, an inner surface, the inner surface defining a hollow sleeve channel, and at least one open end;
    wherein at least a portion of the proximal end of the sleeve body is configured to extend over at least a portion of a proximal end of an insertion portion of a medical speculum;
    wherein the insertion portion comprises an upper bill and a lower bill;
    wherein the sleeve body is configured to receive the upper bill and the lower bill in the hollow sleeve channel configured for visibility and access to a vaginal cavity of a patient by a clinician;
    wherein the sleeve body is configured to expand from a first state to a second state; and
    wherein when the sleeve body is in the first state the proximal end of the sleeve body comprises a gradual broadening of the sleeve body, the gradual broadening of the sleeve body extending beyond the insertion portion of the medical speculum, the gradual broadening of the sleeve body integrally formed with the sleeve body.

2. The sleeve accessory of claim 1, wherein the diameter of the distal end of the sleeve body is between 0.5 and 2.0 inches when in the first state.

3. The sleeve accessory of claim 1, wherein the sleeve body is disposable.

4. The sleeve accessory of claim 1, wherein the sleeve body comprises one or more of the following to assist with adherence of the sleeve body to the insertion portion: gripping elements positioned on the inner surface of the sleeve body, ribbed details, and a texture difference on the inner surface.

5. The sleeve accessory of claim 1, wherein the proximal end of the sleeve body is shaped to conform to the medical speculum.

6. The sleeve accessory of claim 1, wherein the gradual broadening comprises a perforated edge forming a flap, the flap configured to secure the sleeve body to the medical speculum by tucking the flap over a top edge of the medical speculum.

7. The sleeve accessory of claim 1, wherein the sleeve body is made of a rubber or a plastic material.

8. The sleeve accessory of claim 7, wherein the rubber or plastic material is one of a polyisoprene, a polyurethane, a thermoplastic polyurethane, a styrene copolymer, silicone, and a thermoplastic elastomer.

9. The sleeve accessory of claim 1, wherein the sleeve body is coated with at least one of a lubricant, a powder, a surface texture, a bioactive agent, and a therapeutic agent.

10. The sleeve accessory of claim 1, wherein the at least one open end is edged with a ridged finish.

11. The sleeve accessory of claim 1, wherein the sleeve body is made of a transparent material to allow visibility through the sleeve body.

12. The sleeve accessory of claim 1, wherein the sleeve body comprises an open proximal end and a closed distal end.

13. The sleeve accessory of claim 12, wherein the closed distal end further comprises an aperture.

14. The sleeve accessory of claim 1, wherein a delivery cartridge is configured to contain the sleeve body for application to the medical speculum and cover at least a portion of the outer surface of the sleeve body when in the first state.

15. The sleeve accessory of claim 14, wherein the delivery cartridge contains a plurality of sleeves.

16. The sleeve accessory of claim 14, wherein the delivery cartridge is made of a rubber, plastic, or cardboard material.

17. The sleeve accessory of claim 1, wherein the at least one open end comprises one or more of a bead edge, a secondary material attached or adhered to the sleeve body, a different thickness from the sleeve body, and/or a pull tab.

18. A kit comprising:
    a speculum comprising a handle and an insertion portion, the insertion portion comprising an upper bill and a lower bill coupled to the handle; and
    a sleeve accessory comprising:
        a cylindrical sleeve body having a distal end and a proximal end and comprising an outer surface, an inner surface, the inner surface defining a hollow sleeve channel, and at least one open end;
        wherein at least a portion of the proximal end of the sleeve body is configured to extend over at least a portion of a proximal end of the insertion portion of the speculum;
        wherein the sleeve body is configured to receive the upper bill and the lower bill in the hollow sleeve channel;
        wherein the sleeve body is configured to expand from a first state to a second state; and
        wherein when the sleeve body is in the first state the proximal end of the sleeve body comprises a gradual broadening of the sleeve body, the gradual broadening of the sleeve body extending beyond the insertion portion of the speculum, the gradual broadening of the sleeve body integrally formed with the sleeve body.

19. The kit of claim 18, further comprising a plurality of speculums, varying in length, width, and expansion capabilities.

20. The kit of claim 18, further comprising a plurality of sleeve accessories, varying in length and width.

* * * * *